(12) United States Patent
Ericsson et al.

(10) Patent No.: US 6,283,977 B1
(45) Date of Patent: Sep. 4, 2001

(54) STEREOTACTIC APPARATUS

(75) Inventors: Per Ericsson, Solna; Anders Jakobsson, Årsta; Christina Hugosson, Stockholm, all of (SE)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/458,700

(22) Filed: Dec. 13, 1999

(30) Foreign Application Priority Data

Sep. 23, 1999 (SE) .................................... 9903451

(51) Int. Cl.$^7$ .................................................. A61B 19/00
(52) U.S. Cl. ............................................................ 606/130
(58) Field of Search ........................................ 606/130, 1

(56) References Cited

U.S. PATENT DOCUMENTS

| | | | |
|---|---|---|---|
| 3,196,875 | * 7/1965 | Pfeifer ................................ | 606/130 |
| 4,350,159 | * 9/1982 | Gouda ................................ | 606/130 |
| 4,465,069 | * 8/1984 | Barbier et al. ..................... | 606/130 |
| 4,875,478 | * 10/1989 | Chen ................................. | 606/130 |
| 5,649,936 | * 7/1997 | Real .................................. | 606/130 |
| 5,817,106 | 10/1998 | Real . | |
| 5,871,487 | * 2/1999 | Warner et al. ..................... | 606/130 |

OTHER PUBLICATIONS

Leksell Micro–Stereotactic System Product Publication, Elekta Instrument AB, Sweden (1990) pp. 1–11.
Leksell Stereotactic System Product Publication, Elekta Instrument AB, Sweden (1986) pp. 1–20.

* cited by examiner

Primary Examiner—Jeffrey A. Smith
Assistant Examiner—Edvando C. Robert
(74) Attorney, Agent, or Firm—Burns, Doane, Swecker & Mathis L.L.P.

(57) ABSTRACT

A stereotactic apparatus including a support slide for being slidably mounted to an arc, a microdrive unit having an instrument holder for depth adjustment of an instrument along a depth axis, in an essentially arc parallel plane, an arc perpendicular adjusting mechanism for adjustment of the microdrive unit along an arc perpendicular axis, an arc parallel adjusting mechanism for adjustment of the microdrive unit along an arc parallel axis, wherein the arc perpendicular adjusting mechanism includes an arc perpendicular slide, which is movably mounted to the support slide. The arc parallel adjusting mechanism is mounted at an end of the arc perpendicular slide, so that by movement of the arc perpendicular slide in a direction along the arc perpendicular axis the arc parallel adjusting mechanism also moves in that direction. An arc parallel slide is movably mounted to the arc parallel adjusting mechanism, the arc parallel slide being positioned at a different level with respect to the arc perpendicular slide, and the microdrive unit is rigidly mounted with its top portion to the arc parallel slide, and by movement of the arc parallel slide in the arc parallel direction the microdrive unit also moves in the arc parallel direction.

20 Claims, 9 Drawing Sheets

STEREOTACTIC APPARATUS

TECHNICAL FIELD

The present invention relates generally to a stereotactic apparatus for use with a stereotactic frame, for mounting to a skull of a patient and a stereotactic arc mounted to said frame, extending over the skull of the patient, and specifically to a stereotactic apparatus comprising a support slide, slidably mounted to said arc, a microdrive unit comprising an instrument holder for depth adjustment of an instrument along a depth axis, in an arc parallel plane, an arc perpendicular adjusting means for adjustment of the microdrive unit along an arc perpendicular axis, an arc parallel adjusting means for adjustment of the microdrive unit along an arc parallel axis.

BACKGROUND OF THE INVENTION

In neurosurgery a stereotactic frame, for example a Leksell Stereotactic Instrument, is mounted to the skull of a patient to provide fixed references to the brain of the patient. The frame encircles the head of the patient and is mounted with screws to the skull of the patient. On the frame a stereotactic arc is mounted, which crosses over and above the head of the patient. A stereotactic apparatus is slidably mounted on the stereotactic arc via a support slide.

A stereotactic apparatus comprises a microdrive, which comprises an instrument holder, for insertion and withdrawal of an instrument with respect to a target area of the brain of the patient. The microdrive is mounted on top of an X-Y-table for fine adjustment of the instrument along the X and Y-axes. Adjustment of the microdrive at the stereotactic arc makes it possible to achieve parallel insertion paths.

Stereotactic surgery is used, for example, for brain mapping using microelectrodes, brain biopsies, DBS implantation and lesioning.

From U.S. Pat. No. 5,817,106, Real, a stereotactic guide apparatus for use with a neurosurgical headframe is known. The stereotactic guide apparatus is mounted on a slide, which is movable along a stereotactic arc. On top of the slide a platform, comprising an X-Y-table, is mounted. In the platform there is a hole for a tubular instrument guide, through which an instrument, attached to an instrument holder in connection with a microdrive, may be inserted by the microdrive.

A problem with this stereotactic guide apparatus is to be accurate in positioning of the instrument. To obtain accuracy the different parts of the X-Y-table must all have extremely small tolerances.

Another problem is the high postion of the centre of gravity, which makes the apparatus unstable.

A further problem is that the hole through the platform limits the possibility of adjustment along the X- and Y-axes.

A still further problem is that it is extremely difficult to keep the apparatus clean, which is an important factor in surgery.

SUMMARY OF THE INVENTION

It is an aim of the present invention to provide a stereotactic apparatus that is accurate without requiring small tolerances.

Another aim of the present invention is to provide a stereotactic apparatus with improved stability in the construction.

A further aim of the present invention is to provide a stereotactic apparatus with greater possibilities of adjustments.

A still further aim of the present invention is to provide a stereotactic apparatus that is easy to keep clean.

According to these aims and in an aspect of the present invention is a stereotactic apparatus according to the preamble provided which is characterised in that the arc perpendicular adjusting means is an arc perpendicular slide, which is movably mounted to the support slide, the arc parallel adjusting means is mounted at an end of the arc perpendicular slide, so that by movement along the arc perpendicular axis the arc parallel adjusting means also moves in said direction, and comprising an arc parallel slide movably mounted to the arc parallel adjusting means, the arc parallel slide being positioned at a different level with respect to the arc perpendicular slide, and that the microdrive unit is rigidly mounted with its portion that is furthest apart from the patient to the arc parallel slide, and by movement of the slide in the arc parallel direction the microdrive also moves in said direction.

The adjustment in the arc perpendicular and arc parallel direction is carried out in different planes and so is the depth adjustment.

These features give the advantages that it is easy to reach all the parts of the stereotactic apparatus and it is easier for a surgeon to survey what he/she is doing.

Further advantages is that the centre of gravity is much closer to the patient, which provides a more stabilised construction, and the path for the instrument is shorter, which minimise angle deviation of the instrument path.

In one embodiment of the present invention the instrument holder comprises an arm which is moved by the microdrive in a governed motion along the depth axis.

Said arm is preferably turnable aside for easy mounting and demounting of an instrument or a cannula and easy access to the microdrive and its inner parts.

In another embodiment of the invention, the microdrive preferably comprises a motor, which through a gear drives a screw on which the instrument holder is provided for a governed motion along the screw, which is orientated along the depth axis.

In a further embodiment of the invention, a screw in a motorised microdrive may also be manoeuvred manually by turning a knob connected to an extended axle of the motor. This has the advantage that an instrument always can be manually manoeuvred, even if, for example, there will be a power failure.

Preferably, in another embodiment of the invention, a gear changes the ratio between an extended axle of a motor and a screw, both positioned in a motorised microdrive, so that the screw rotates with a speed different to that of the axle of the motor for accurate depth adjustment and also reverses the rotational direction of the screw, which transfers a manual rotation of the extended axle of the motor to a logical movement of the instrument holder.

In a further embodiment of the present invention a fixed guide for an instrument may be provided at the portion of the microdrive that is closest to the patient. This is for guiding of an instrument.

In another embodiment of the invention, if a cannula is used, cannula adjusting means may be provided in a fixed guide on the microdrive for adjustment of the cannula along the depth axis. The cannula adjusting means makes it possible to adjust the position of the cannula tip in respect to a target point in the brain and thus how much of the instrument that should extend from the cannula.

Preferably, in a still further embodiment of the invention, a settable guide for an instrument, which has a guide member, is settable mounted along the depth axis by means of a slide and a fixing screw at the microdrive so that the guide member can be provided between the microdrive and the patient. The advantage is that a guide can be positioned close to the skull of the patient for a more precise guiding of an instrument, independently of the mounting of the stereotactic frame.

As will be evident to a person skilled in the art these different embodiments may be used one by one or combined in any arbitrary way.

These and other embodiments and advantages of the present invention will be evident from the appended claims and the following description.

BRIEF DESCRIPTION OF THE DRAWINGS

Some preferred embodiments of the invention are illustrated in the accompanying drawings, in which:

FIG. 7b illustrates the cannula adjusting means in a cross-section view along the lines I-I in FIG. 7a.

DETAILED DESCRIPTION OF PREFERRED EMBODIMENTS OF THE INVENTION

Figure 1:
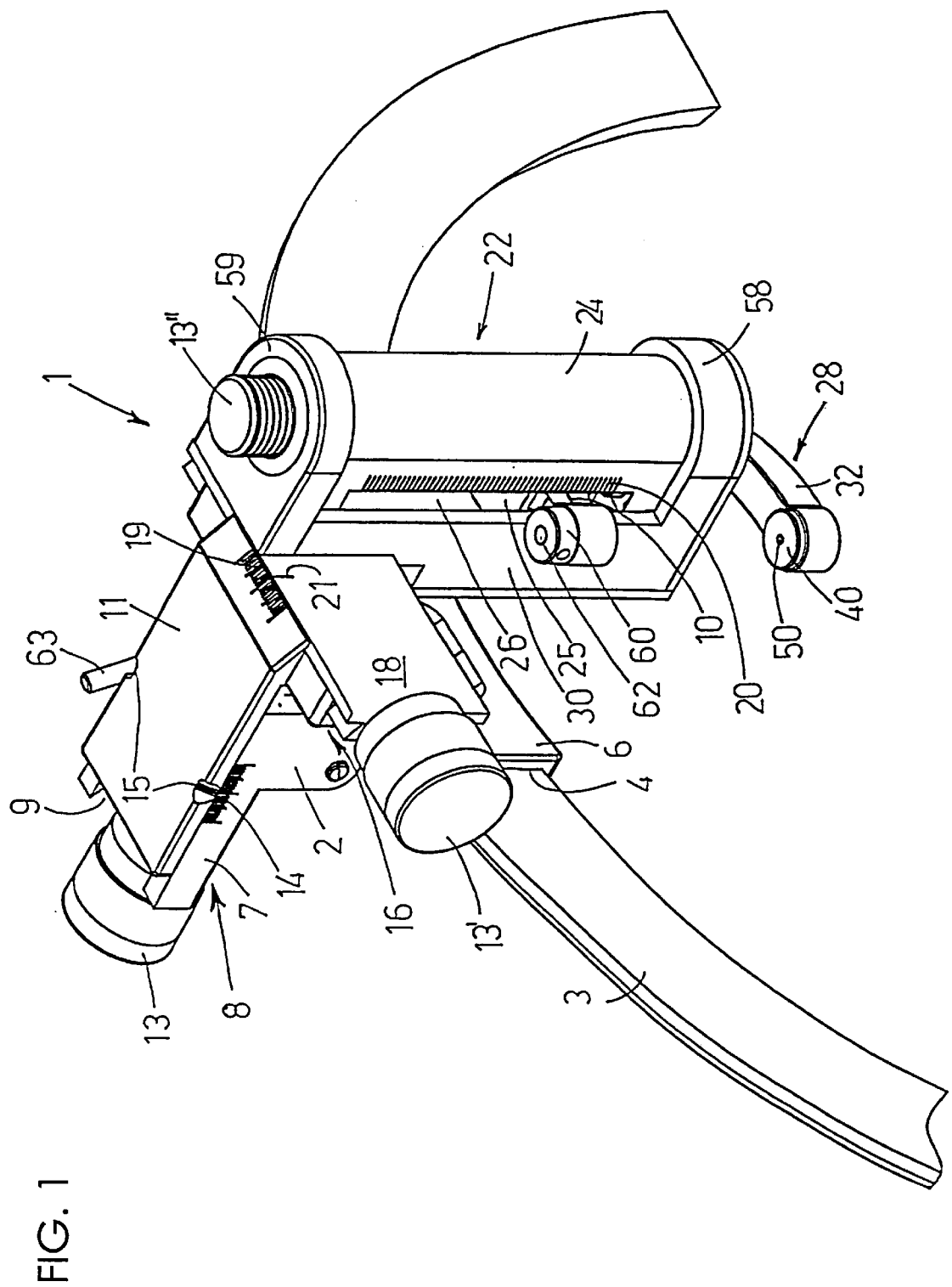
FIG. 1 illustrates a first embodiment of the present invention in a perspective view.
Figure 2:
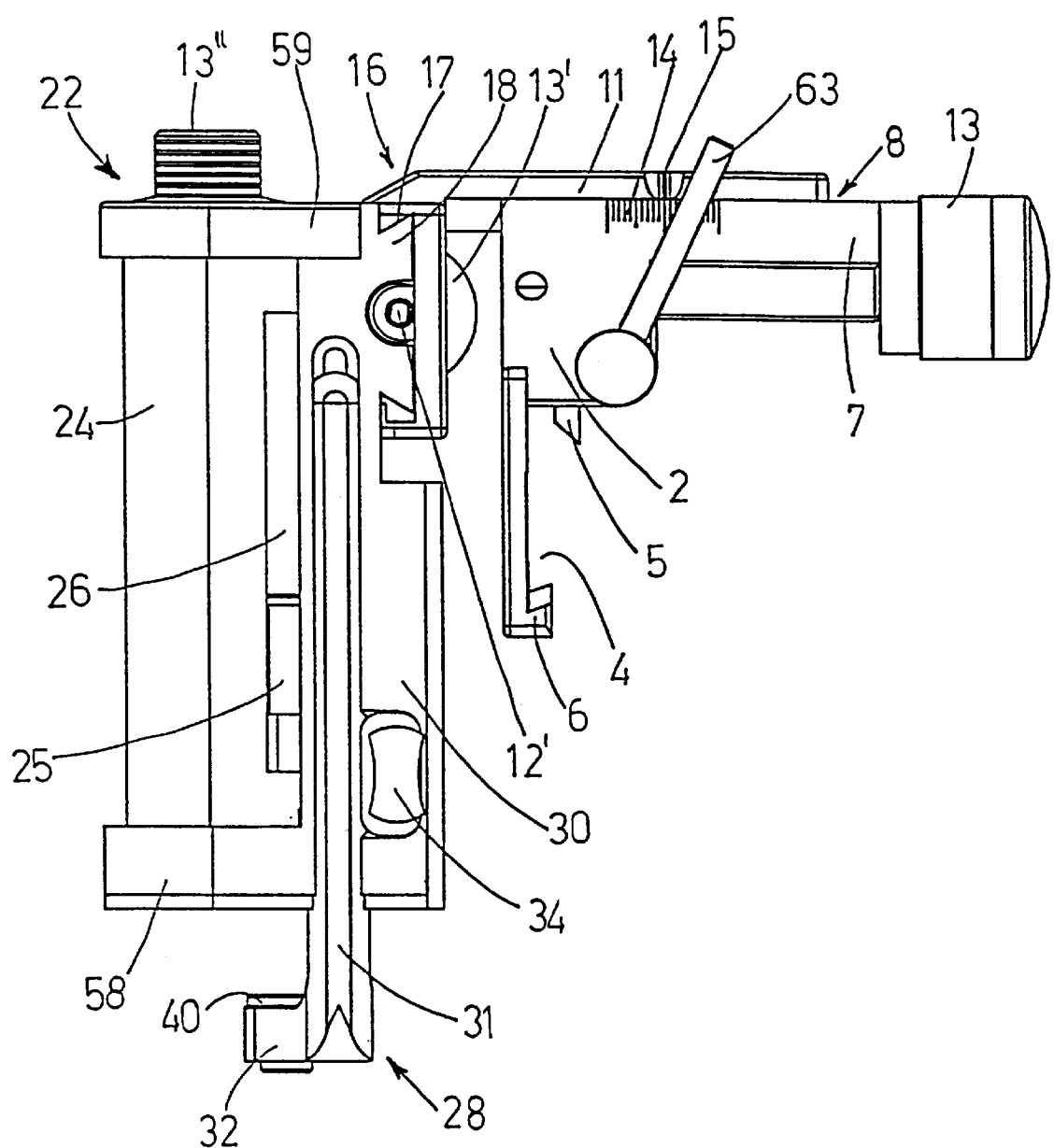
FIG. 2 illustrates the first embodiment of the present invention in a plan view from the side that is hidden in FIG. 1.
Figure 3:
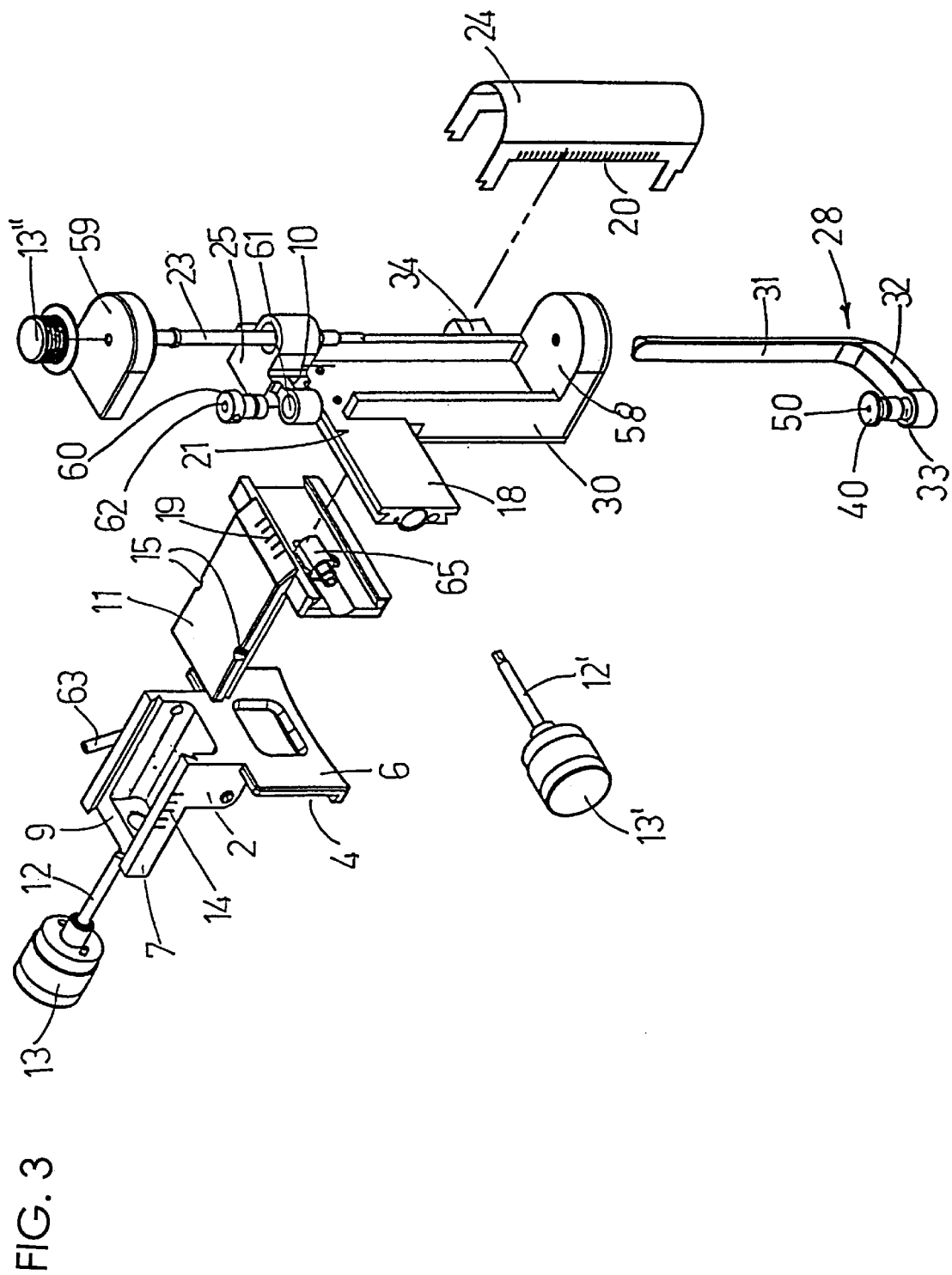
FIG. 3 illustrates the first embodiment of the present invention in an exploded view.

According to a first embodiment of the present invention the stereotactic apparatus 1 comprises a support slide 2 for slidable mounting to a stereotactic arc 3. See FIGS. 1, 2 and 3. The stereotactic arc 3 is mounted to a stereotactic frame (not shown), preferably of the type Leksell Stereotactic Instrument. The support slide 2 has a lower portion 6 wherein the stereotactic arc 3 can slide in an arcuate recess 4. A movable bracket 5 may be used for the fixation of the support slide 2 on the arc 3. In this case a lever 63 is turned so that an excenter presses the bracket 5 against the stereotactic arc 3. See FIG. 2. The upper portion 7 of the support slide 2 protrudes 90 degrees from the lower portion 6, almost like an upside down L.

The upper portion 7 comprises arc perpendicular adjusting means 8, which comprise a recess 9 along an arc perpendicular axis for supporting an arc perpendicular slide 11. The arc perpendicular slide 11 is movably mounted in the recess 9 of the upper portion 7 of the support slide 2 and is movable in a governed motion by means of a screw 12, which has a turning knob 13. The arc perpendicular slide 11 has a nut arrangement 65 (hidden in FIG. 3) for engagement with the screw 12.

Preferably a playfree screw arrangement is used, for example a lengthwise split nut arrangement 65 with an internal thread that is provided with a radial spring or a ball screw.

The arc perpendicular slide 11 is preferably designed as a dovetail and the recess 9 has a corresponding shape. Of course other shapes of the slide and recess could be used. To demount the arc perpendicular slide 11 from the recess 9, the screw 12 is rotated until the arc perpendicular slide 11 screws off the support slide 2. As would be evident for a person skilled in the art the arc perpendicular slide 11 could be moved in the recess by other means.

Along the upper portion 7 of the support slide 2, preferably on both sides, there is a scale 14 provided and on the arc perpendicular slide 11 is a notch 15, preferably arranged on both sides, which co-operates with the scale 14 so that the arc perpendicular position and thus the displacement is readable. Of course the scale 14 and notch 15 may be provided vice versa.

At the end of the arc perpendicular slide 11, which is opposite the knob 13, arc parallel adjusting means 16 are provided. Thus, the arc parallel adjusting means 16 moves together with the arc perpendicular slide 11. The arc parallel adjusting means 16 extends lengthwise along an arc parallel axis and is suspended at the end of the arc perpendicular slide 11, "hanging down", and comprise a recess 17 along the arc parallel axis for an arc parallel slide 18.

The arc parallel slide 18 is movably mounted in the recess 17 of the arc parallel adjusting means 16 and is movable in a governed motion preferably by means of a screw 12', which has a turning knob 13' in one of its ends and is mounted in the arc parallel slide 18.

The screw 12' is preferably playfree and engages with a nut arrangement 65 provided in the recess 17 of the arc parallel adjusting means 16. The nut arrangement 65 is split lengtwise and is provided with a radial spring.

The arc parallel slide 18 is also preferably designed as a dovetail and the recess 17 has a corresponding shape. To demount the arc parallel slide 18 from the recess 17, the screw 12 is rotated until the arc parallel slide 18 screws off the slide 11.

Along the end of the arc perpendicular slide 11 that holds the arc parallel adjusting means 16 there is a scale 19 and in the arc parallel slide 18 there is a notch 21, which is co-operating with the scale 19 so that the arc parallel postion and thus the displacement is readable. Of course the scale and notch may be provided vice versa.

A microdrive 22 unit is, at its upper portion, fixedly attached to the arc parallel slide 18, for depth adjustment of an instrument along the depth axis. The depth axis is preferably positioned in an arc parallel plane but the depth axis may optionally be positioned in a plane angular to the arc 3. Thus, the arc parallel slide 18 moves together with the microdrive unit 22. In this way a position of the microdrive unit 22 is adjustable both in the arc perpendicular direction and in the arc parallel direction (and along the arc 3).

The knobs 13, 13' are preferably "child proof", i.e. they need to be pushed in before they connect for turning of the screw 12, 12'.

The microdrive unit 22, extending along the depth axis, comprises a back support 30 with an integrated bottom 58, a front casing 24 and a top 59 provided with a turning knob 13" ("child proof", too), which is connected to a screw 23, for example a ball screw, journalled in the top 59 and in the bottom 58 of the microdrive unit 22 and positioned between the back support 30 and front casing 24 of the microdrive 22. On the screw 23 an instrument holder 25 is provided for a governed motion along the depth axis.

The front casing 24 is demountable to allow easy access to the inner parts and easy cleaning and also shields the inner of the microdrive unit 22. The front casing 24 is inserted in slits (not shown) in the back support 30.

By turning the knob 13" the instrument holder 25 moves along the screw 23, either upwards or downwards depending on which way the knob 13 is turned. The instrument holder 25 protrudes out of a slot 26 between the front casing 24 and the back support 30, which is rigidly attached at its upper portion to the arc parallel slide 18.

Figure 9:
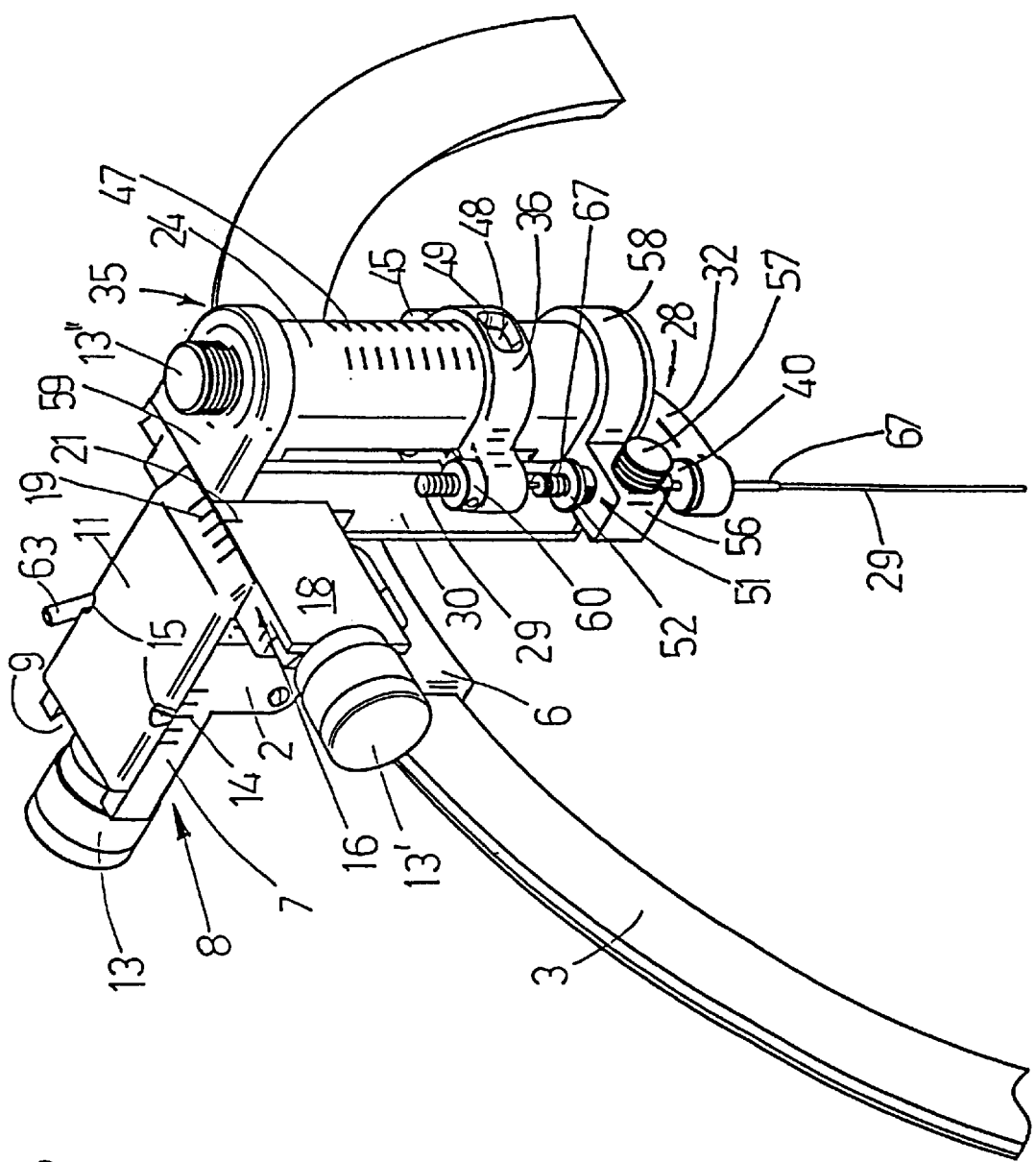
FIG. 9 illustrates the fourth embodiment of the present invention with an instrument mounted.

At the outer end of the instrument holder 25 an instrument 29 (only shown in FIG. 9) may be attached preferably by means of a exchangeable holder member 60, which is pressfitted into a hole 61 in the instrument holder 25. An example of an instrument 29 is shown in FIG. 9.

The exchangeable holder member 60 has a hole 62 adapted for the chosen instrument and the friction forces between the walls of the hole 62 and the instrument retains the instrument.

But as is evident for a person skilled in the art the fixing of the instrument 29 in the instrument holder 25 can be achieved in a lot of different ways, for example, by a spring biased tongue or a fixing screw. The instrument 29 may by use of the microdrive 22 be inserted or withdrawn from the brain of the patient.

The front casing 24 is provided with a scale 20 at the edge of the slot 26 and the instrument holder 25 is provided with a notch 10 where the instrument holder 25 protrudes from the slot 26 for co-operation with the scale. In this way the depth position and thus the displacement of the instrument is readable.

A settable instrument guide 28 for guiding the instrument 29 along the accurate path is settable mounted to the microdrive unit 22. The settable instrument guide 28 has a leg portion 31, extending in the depth direction, which has a cross section shape, for example a dovetail shape, that corresponds with the mounting (see FIG. 2) on the microdrive unit so that the settable instrument guide cannot rotate, but is slidable in the depth direction, and an arm 32 extending orthogonally from the leg portion 31.

A fixing screw 34, provided in the microdrive unit 22, fixes the settable instrument guide 28 at a level between the lower portion of the microdrive unit 22 and the skull of the patient by tightening the fixing screw 34 against the leg portion 31. Of course the settable instrument guide 28 could instead be set by means of, for example, a spring biased tongue.

In the arm 32 a hole 33, which is align with the instrument attachment, is situated for receiving a part of the instrument 29. Preferably, the hole 33 is big enough to be able to receive an exchangeable guide member 40 provided with a hole 50, which size is adapted for a chosen instrument.

Figure 4:
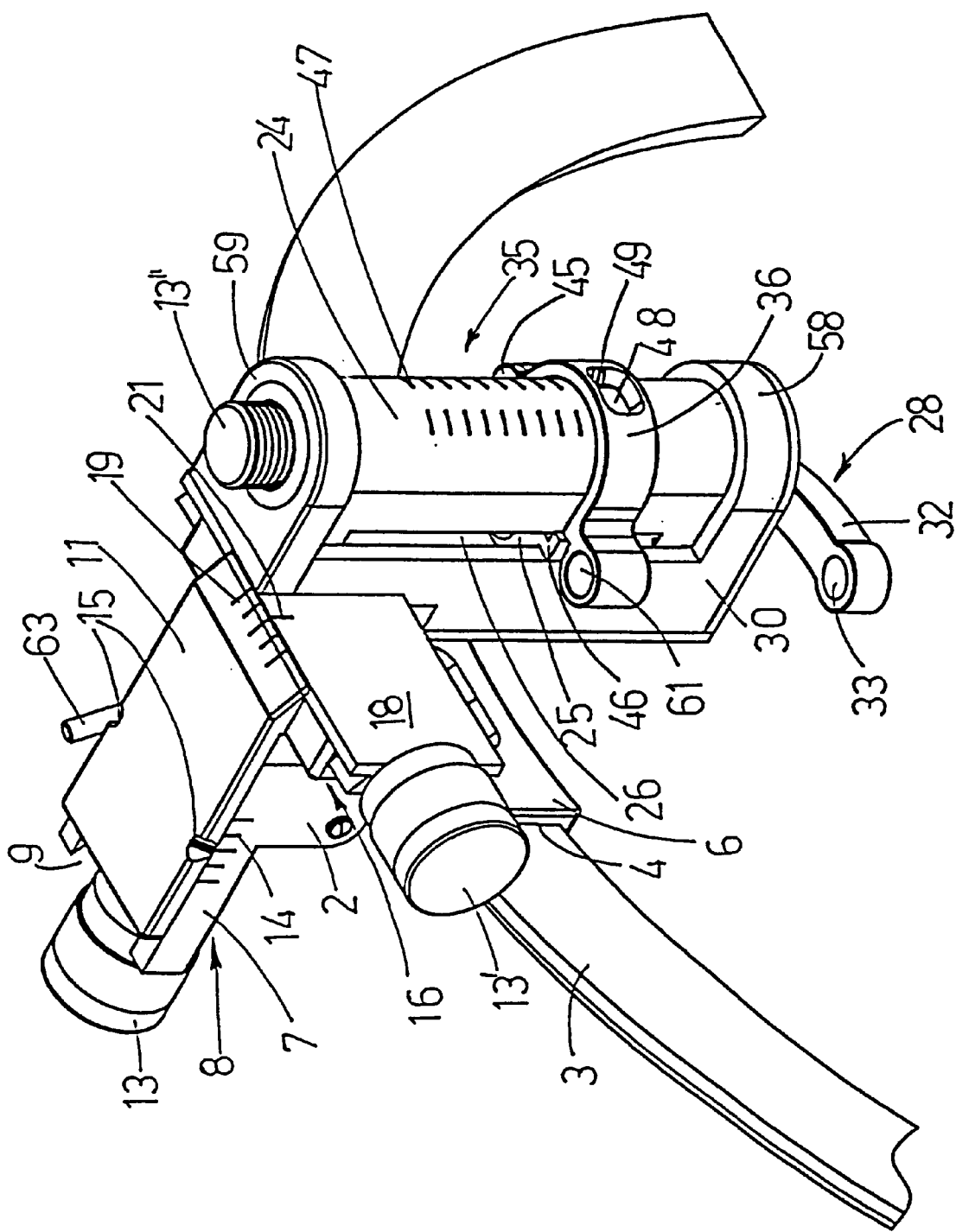
FIG. 4 illustrates a second embodiment of the present invention in a perspective view.

According to a second embodiment of the invention, see FIG. 4, the stereotactic apparatus comprises a support slide 2, arc perpendicular adjusting means 8, arc parallel adjusting means 16 and a settable instrument guide 28 as described in the first embodiment.

Figure 5:
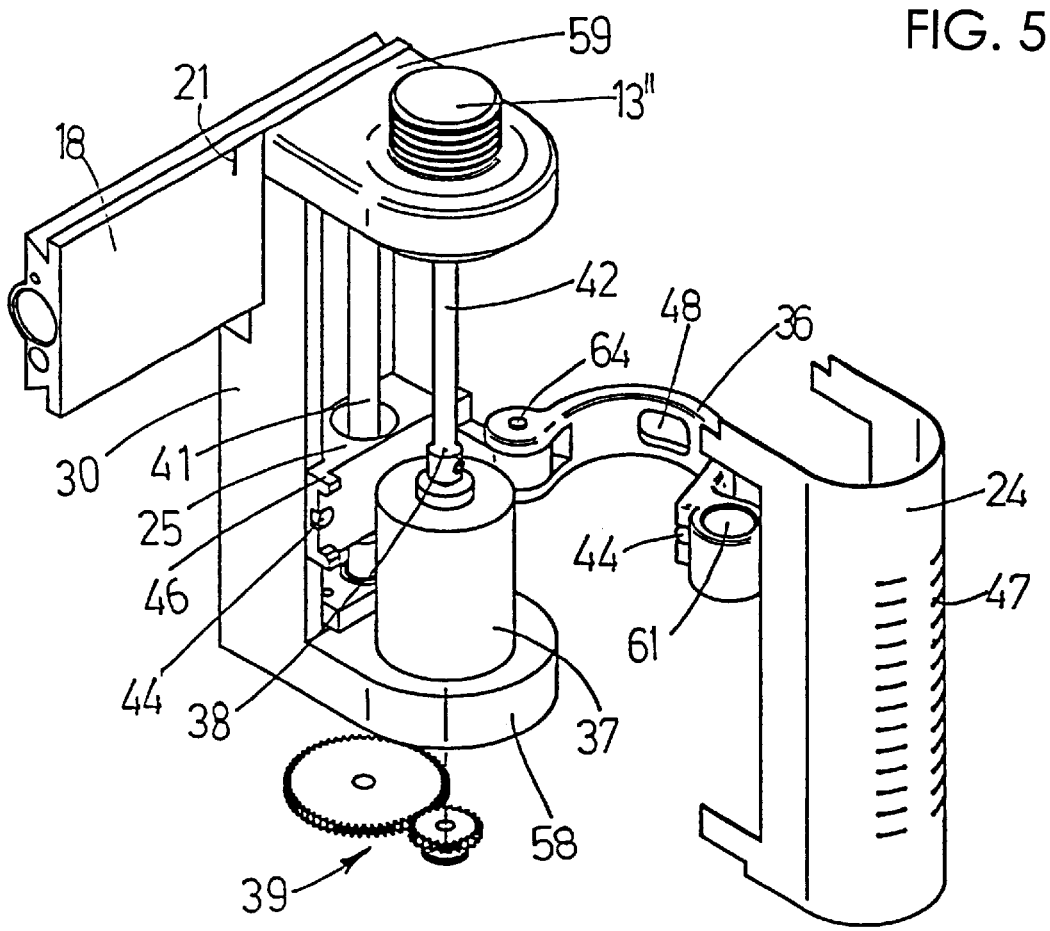
FIG. 5 illustrates a motorised microdrive in an exploded view.

Also in this embodiment there is a microdrive unit 35, see FIG. 5, rigidly attached to the arc parallel slide 18, but it is motorised. The microdrive unit 35 comprises a front casing 24, which is demountable to allow easy reach of the inner parts and easy cleaning, and a back support 30, which is at its upper portion fixedly attached to the arc parallel slide 18. The front casing 24 also shields the inner of the microdrive 35. A top 59 and a bottom 58 are provided, too.

Further, the microdrive unit 35 comprises a motor 37 mounted on the bottom 58 and having a motor axle 38, which has an extension 42, a gear 39, shielded in the bottom 58, and a screw 41, for example a ball screw. The motor axle 38, with its extension 42, and the screw 41 are parallel and extend along the depth axis inside the microdrive unit 35 and both are journalled in the top 59. The gear is provided at the bottom of the microdrive unit 35.

The motor 37 drives the screw 41 via the gear 39. The gear 39 both reverses the rotational direction of the screw 41 and changes the ratio between the motor axle 38 and the screw 41 so that the screw 41 rotates with a speed different to that of the motor axle 38 (eg slower).

An instrument holder 25 is engaged to the screw 41 for governed motion along the screw 41. In order to avoid rotation of the instrument holder 25 around the screw 41 the instrument holder 25 has a planar surface adapted to abut and slide along the walls of the back suport 30.

The instrument holder 25 protrudes out of two slots 26, arranged on respective side of the microdrive unit 35, between the front casing 24 and the back support 30.

The instrument holder 25 comprises preferably an arm 36, which is hingably, at 64, connected to one of the protruding portions 45 of the instrument holder 25. Said arm 36 is in its working position situated along the outside of the front casing 24, orthogonally to the depth axis, and adjoins the other protruding portion 46 of the instrument holder 25 and is releasably fixed, e.g. by means of a magnetic lock 44.

At the free end of the arm 36 an instrument 29 may be attached preferably by means of an exchangeable holder member 60 (not shown in FIGS. 4 and 5, but shown in FIG. 9), which is pressed into a hole 61 in the instrument holder 25. The exchangeable holder member 60 has a hole 62 adapted for the chosen instrument and the friction forces between the walls of the hole 62 and the instrument retains the instrument.

But as is evident for a person skilled in the art the fixing of the instrument 29 in the instrument holder 25 can be achieved in a lot of different ways, for example, by a spring-biased tongue or a fixing screw.

The arm 36 is turnable aside owing to the hinge 64 for easy attachment/detachment of an instrument 29 or a cannula 67 and this also makes it possible to detach the front casing 24.

Preferably, on the front of the front casing 24 a scale 47 is provided and there is a hole 48 in the arm 36 so that the scale 47 is visable through the hole 48. A notch 49 is provided in the arm 36 at the side of the hole 48 for co-operation with the scale 47. In this way the depth position and thus the displacement of the instrument is readable. Of course two notches 49, one on respective side, could also be provided.

The extension 42 of the motor axle 38 is, at its end, provided with a turning knob 13" for manually manoeuvring of the screw 41 via the gear 39. Also this knob is "child proof". By turning the knob 13" the instrument holder 25 moves along the screw 41, either upwards or downwards depending on which way the knob 13" is turned.

The instrument 29 may either be inserted or withdrawn from the brain of the patient by motor or manually.

Preferably the motor 37 is controlled by means of a remote control (not shown) or by hydraulic means (not shown), because then no forces are supplied to the arc that could interrupt the settings of the arc during the surgery and the surgeon may freely move around the patient and thus have a better view over, for example, reactions of the patient.

Also this embodiment is optionally provided with a settable instrument guide 28 as described in the first embodiment.

Figure 6:
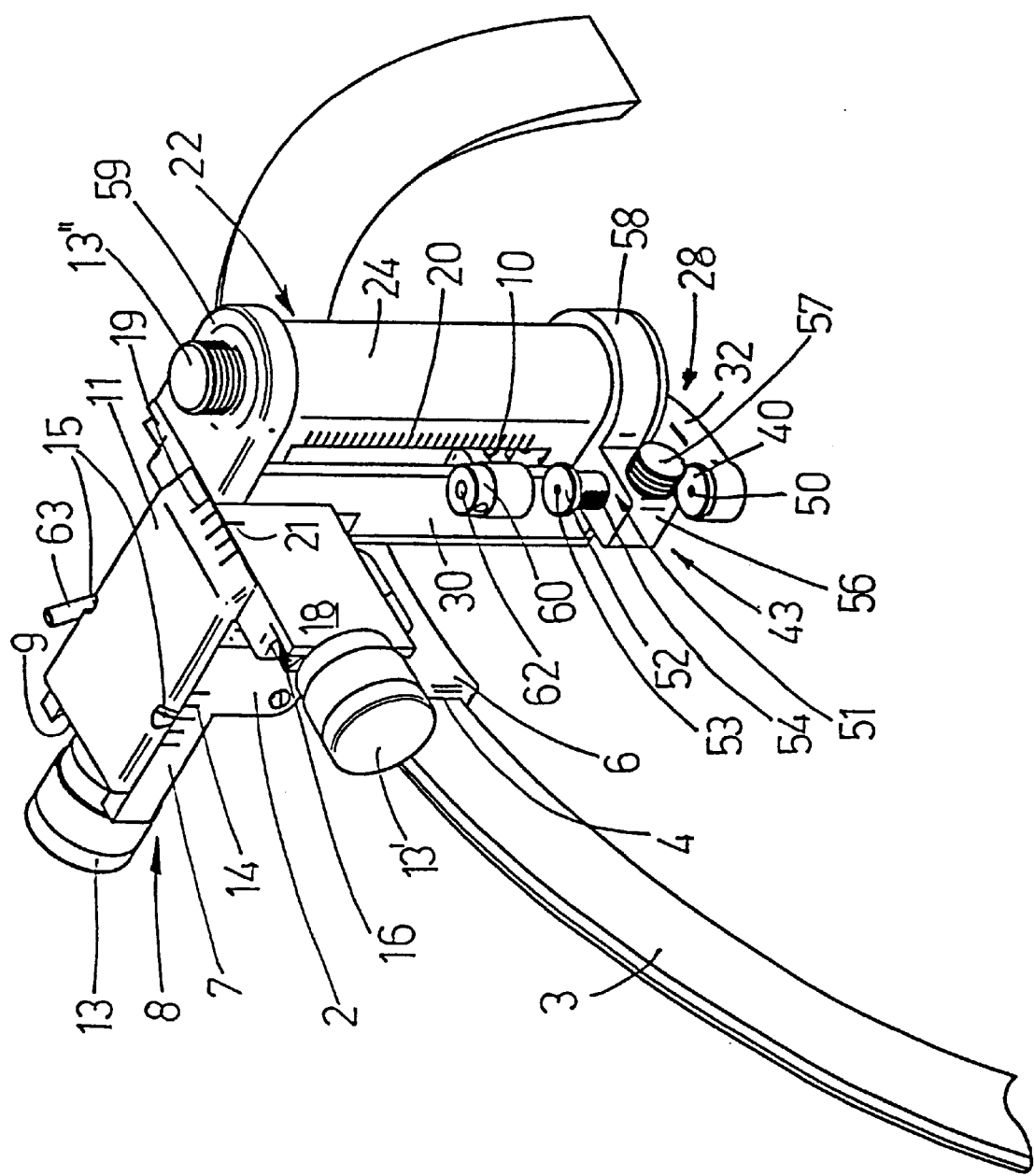
FIG. 6 illustrates a third embodiment of the present invention in a perspective view.

According to a third embodiment of the invention, see FIG. 6, the stereotactic apparatus comprises a support slide 2, arc perpendicular adjusting means 8, arc parallel adjusting means 16, a manual microdrive unit 22 and a settable instrument guide 28 as described in the first embodiment.

At the lower portion of the microdrive unit 22 a fixed instrument guide 43 is provided. Said fixed instrument guide 43 is align with the attachment for the instrument 29 (see FIG. 9) and the previously described settable instrument guide 28 so that an instrument guide path is made up.

With this arrangement there is not any need for a cannula or a guiding tube. For example, a guiding member 40, like the one that is used in the settable instrument guide 28 (see FIG. 1) could be used.

Figure 7A:
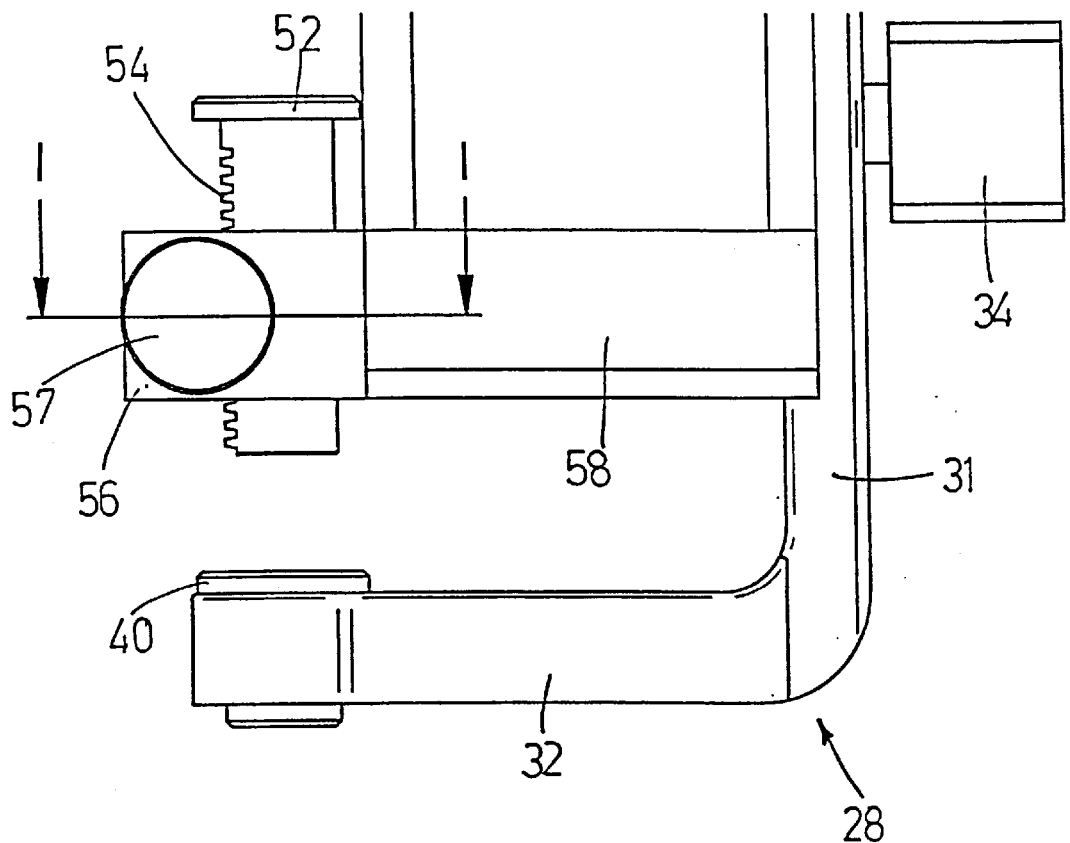
FIG. 7a shows a close-up view of a part of the third embodiment of the present invention, which comprises cannula adjusting means.
Figure 7B:
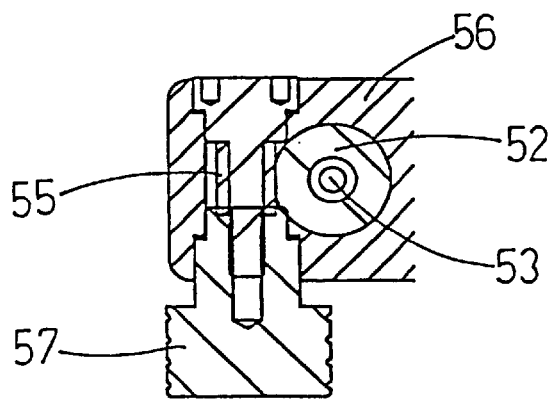

Some instruments are although used in co-operation with a cannula 67, see FIG. 9. For this reason special cannula adjusting means 51 are provided. See FIG. 7. Said cannula adjusting means 51 comprises a base member 56, through which, along the depth axis, a cannula guide portion 52 is provided, and a pinion 55.

The pinion 55 is provided in the base member 56, orthogonally to the depth axis, and is provided with a turning knob 57. The cannula guide portion 52 is provided with a hole 53 adapted for the cannula 67 and a rack 54 for engagement with the pinion 55.

By turning of the knob 57 the pinion 55 urges the cannula guide portion 52 to move upwards or downwards in the depth direction, depending on the rotational direction of the turning of the knob 57. The cannula guide portion 52 may be exchangeable to be able to receive cannulas of different widths.

Figure 8:
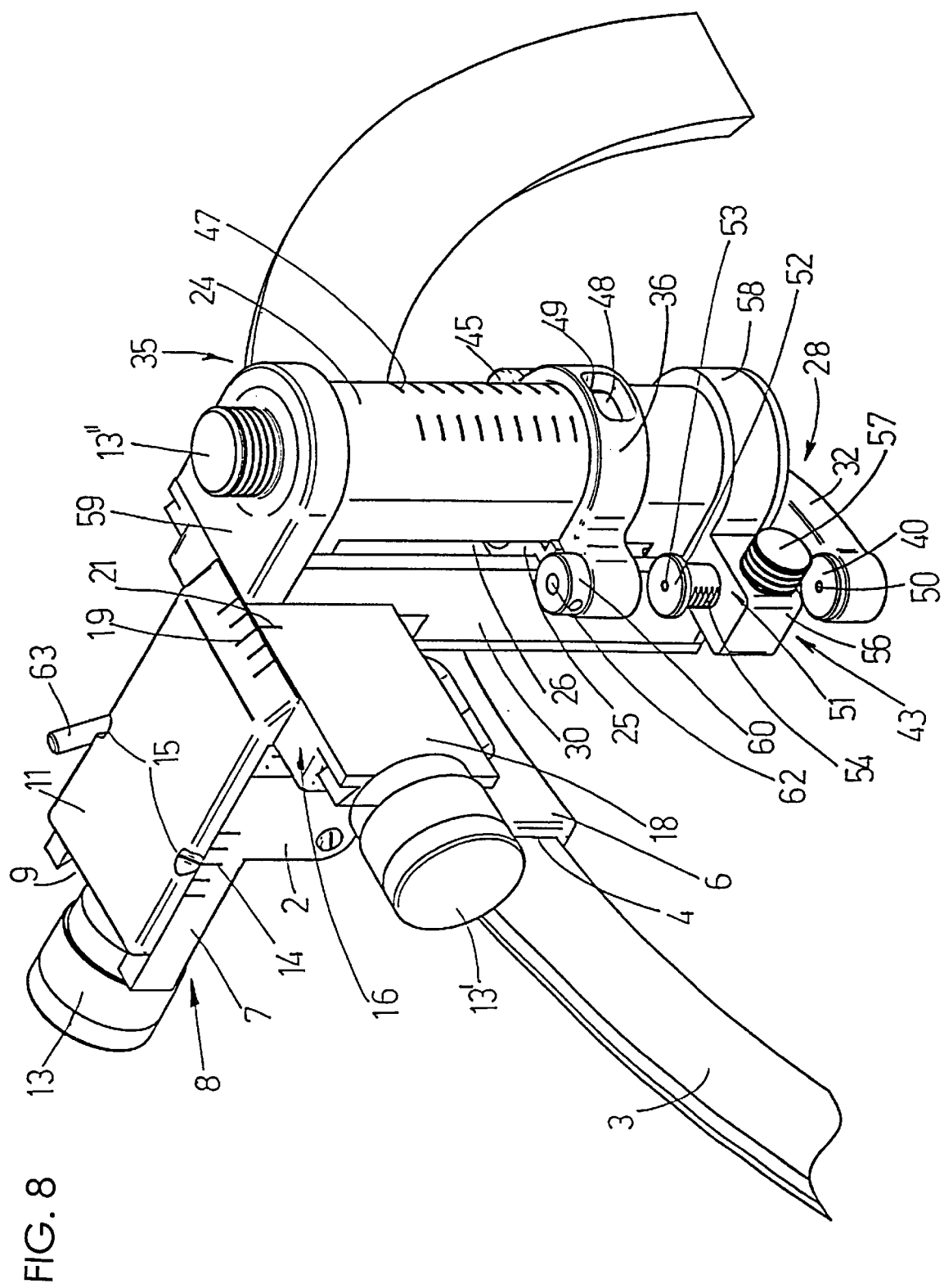
FIG. 8 illustrates a fourth embodiment of the present invention in a perspective view.

According to a fourth embodiment of the invention, see FIG. 8, the stereotactic apparatus comprises a support slide 2, arc perpendicular adjusting means 8, arc parallel adjusting means 16 and a settable instrument guide 28 as described in the first embodiment. Further the stereotactic apparatus comprises a motorised microdrive unit 35 as described in the second embodiment and a fixed instrument guide 43, with cannula stop means 51, as described in the third embodiment.

The fourth embodiment of the stereotactic apparatus 1 may, for example, be used as follows (see FIG. 9). As is evident for the person skilled in the art the use is different for different instruments and purposes.

The references of the target point are set and the stereotactic frame (not shown) and the stereotactic arc 3 is mounted and set in the proper position. A burr hole is then made in the skull of the patient.

The stereotactic apparatus 1 is mounted on the stereotactic arc 3 and adjusted to the proper position by the arc perpendicular adjusting means 8 and the arc parallel adjusting means 16 and then the settable instrument guide 28 is set as close as possible to the skull of the patient.

A guide member 40 is mounted in the settable instrument guide 28 having a hole 50 that corresponds with the chosen instrument or cannula, if used, and a holder member 60 is mounted in the instrument holder 25 having a hole 62 that corresponds with the chosen instrument.

Cannula adjusting means 51 is mounted in the fixed instrument guide 43 if a cannula 67 is used. Otherwise a guide member 40 with a hole 50 that corresponds with the chosen instrument is mounted.

The arm 36 of the instrument holder 25 is turned aside and a cannula 67 is inserted, if used, through the hole 53. Then the arm 36 is turned into working position and the instrument 29 is inserted through the hole 62, through the cannula adjusting means 51 and the possible cannula 67 and through the hole 50 of the guide member 40 in the settable instrument guide 28 and finally the instrument 29 is set in the instrument holder 25, for example by a screw as earlier mentioned.

Now the instrument 29 can be inserted along the depth axis in the brain either manually or by operating the motor 37.

Afterwards the instrument is detached or at least withdrawn from the brain and the position may be changed by turning the knobs 13, 13' on the arc perpendicular adjusting means 8 and the arc parallel adjusting means 16, respectively. Then the operation can be repeated in a parallel instrument insertion path.

As is evident from the text above and figures the arc perpendicular, arc parallel and depth adjustment directions are situated in different planes. The slides 11, 18 are easily demounted and designed in a smooth fashion and the front casing 24 are likewise easily demounted to provide an apparatus that is easy to keep clean.

The front casing 24 together with the back support 30 and the top 59 and bottom 58 members shield the inner parts of the microdrive unit 22, 35 from being contaminated. For that reason a seal may be provided in the slots 26 and/or is a sealing element arranged on the instrument holder 25 moving together with the instrument holder 25, e.g. flexible stripes or bellows.

What is claimed is:

1. A stereotactic apparatus for use with a stereotactic frame, for mounting to a skull of a patient, and a stereotactic arc mounted to said frame, extending over the skull of the patient, said stereotactic apparatus comprising:

a support slide, for being slidably mounted to the arc, a microdrive unit comprising an instrument holder for depth adjustment of an instrument along a depth axis, in an essentially arc parallel plane, an arc perpendicular adjusting means for adjustment of the microdrive unit along an arc perpendicular axis, an arc parallel adjusting means for adjustment of the microdrive unit along an arc parallel axis, wherein the arc perpendicular adjusting means comprises an arc perpendicular slide, which is movably mounted to the support slide, the arc parallel adjusting means is mounted at an end of the arc perpendicular slide, so that by movement of the arc perpendicular slide in a direction along the arc perpendicular axis the arc parallel adjusting means also moves in said direction, and an arc parallel slide movably mounted to the arc parallel adjusting means, the arc parallel slide being positioned at a different level with respect to the arc perpendicular slide, wherein the microdrive unit is rigidly mounted with its top portion to the arc parallel slide, and by movement of the arc parallel slide in the arc parallel direction the microdrive unit also moves in said arc parallel direction.

2. The stereotactic apparatus of claim 1, wherein the instrument holder engages with a screw and slides along at least one inner wall of the microdrive unit for movement in a governed motion along the depth axis.

3. The stereotactic apparatus of claim 2, wherein said instrument holder is provided with a hingably attached arm, which is turnable aside for easy access when mounting/demounting an instrument or a cannula.

4. The stereotactic apparatus of claim 3, wherein the microdrive unit comprises a motor, which through a gear drives the screw with which the instrument holder is engaged for governed motion along said screw, which is orientated along the depth axis.

5. The stereotactic apparatus of claim 2, wherein the microdrive unit comprises a motor, which through a gear drives the screw with which the instrument holder is engaged for governed motion along said screw, which is orientated along the depth axis.

6. The stereotactic apparatus of claim 1, wherein said instrument holder is provided with a hingably attached arm, which is turnable aside for easy access when mounting/demounting an instrument or a cannula.

7. The stereotactic apparatus of claim 6, wherein the microdrive unit comprises a motor, which through a gear drives the a screw with which the instrument holder is engaged for governed motion along said screw, which is orientated along the depth axis.

8. The stereotactic apparatus of claim 1 wherein the microdrive unit comprises a motor, which through a gear drives a screw with which the instrument holder is engaged for governed motion along said screw, which is orientated along the depth axis.

9. The stereotactic apparatus of claim 8, wherein the screw for movement of the instrument holder may be maneuvered manually by turning a knob connected to an extended axle of the motor.

10. The stereotactic apparatus of claim 9, wherein said gear changes a ratio between an axle of the motor and the screw so that the screw rotates with a speed different to that of the axle of the motor.

11. The stereotactic apparatus of claim 9, wherein said gear reverses a rotational direction of the screw vis-a-vis the motor.

12. The stereotactic apparatus of claim 8, wherein said gear changes a ratio between an axle of the motor and the screw so that the screw rotates with a speed different to that of the axle of the motor.

13. The stereotactic apparatus of claim 12, wherein said gear (39) reverses a rotational direction of the screw vis-a-vis the motor.

14. The stereotactic apparatus of claim 8, wherein said gear reverses a rotational direction of the screw vis-a-vis the motor.

15. The stereotactic apparatus of claim 1, wherein a fixed guide for an instrument is provided at a portion of the microdrive unit that is closest to the patient.

16. The stereotactic apparatus of claim 15, wherein cannula adjusting means are provided in the fixed guide for adjustment of a cannula along the depth axis.

17. The stereotactic apparatus of claim 16, wherein the cannula adjusting means is movable along the depth axis by means of a rack and a pinion.

18. The stereotactic apparatus of claim 1, wherein a settable guide for the instrument with a guide member is settably mounted along the depth axis by means of a slide and a fixing screw at the microdrive unit so that said guide member is arranged between the microdrive and the patient.

19. The stereotactic apparatus of claim 1, wherein the arc parallel slide and the arc perpendicular slide are dovetail slides.

20. The stereotactic apparatus of claim 1, wherein the arc parallel slide and the arc perpendicular slide each are connected to a screw for manual movement by rotating a knob provided at the screw.

* * * * *